United States Patent
Wang et al.

(10) Patent No.: US 12,390,186 B2
(45) Date of Patent: Aug. 19, 2025

(54) ULTRASOUND-INDUCED POSITIONING TYPE PUNCTURE ASSEMBLY AND SLEEVE TYPE SMALL NEEDLE KNIFE

(71) Applicant: Beijing Longfu Hospital, Beijing (CN)

(72) Inventors: Yuanli Wang, Beijing (CN); Qingpu Wang, Beijing (CN); Yanli Lu, Beijing (CN); Zhijun Tian, Beijing (CN)

(73) Assignee: BEIJING LONGFU HOSPITAL, Beijing (CN)

( * ) Notice: Subject to any disclaimer, the term of this patent is extended or adjusted under 35 U.S.C. 154(b) by 918 days.

(21) Appl. No.: 17/596,591

(22) PCT Filed: Jun. 12, 2020

(86) PCT No.: PCT/CN2020/095853
§ 371 (c)(1),
(2) Date: Dec. 14, 2021

(87) PCT Pub. No.: WO2020/249093
PCT Pub. Date: Dec. 17, 2020

(65) Prior Publication Data
US 2022/0304648 A1    Sep. 29, 2022

(30) Foreign Application Priority Data

Jun. 14, 2019 (CN) .......................... 201920896328.4
Jun. 14, 2019 (CN) .......................... 201920897676.3

(51) Int. Cl.
| | | |
|---|---|---|
| A61B 8/08 | (2006.01) | |
| A61B 10/02 | (2006.01) | |
| B26D 1/62 | (2006.01) | |
| B26D 7/26 | (2006.01) | |

(52) U.S. Cl.
CPC ........ *A61B 8/0833* (2013.01); *A61B 10/0233* (2013.01); *B26D 1/626* (2013.01); *B26D 7/26* (2013.01)

(58) Field of Classification Search
None
See application file for complete search history.

(56) References Cited

U.S. PATENT DOCUMENTS

| | | | |
|---|---|---|---|
| 9,566,189 B2* | 2/2017 | Morlet | ................ A61F 9/00745 |
| 9,592,352 B2* | 3/2017 | Matsuzawa | ........... A61M 5/329 |
| 9,980,699 B2* | 5/2018 | Quearry | ............ A61B 10/0233 |
| 2017/0055961 A1 | 3/2017 | Ryan | |

FOREIGN PATENT DOCUMENTS

| | | |
|---|---|---|
| CN | 206714805 U | 12/2017 |
| CN | 207384309 U | 5/2018 |
| CN | 109259834 A | 1/2019 |
| CN | 208404835 U | 1/2019 |
| CN | 210472185 U | 5/2020 |

* cited by examiner

*Primary Examiner* — Manuel A Mendez
(74) *Attorney, Agent, or Firm* — Shumaker, Loop & Kendrick, LLP

(57) ABSTRACT

An ultrasound-induced positioning type puncture assembly and a sleeve type small needle knife are provided. The small needle knife includes a cutting assembly and a puncture assembly. The puncture assembly includes a puncture needle core and a puncture sleeve; an annular groove facing an ultrasound equipment probe is formed in an outer wall of the puncture sleeve along a circumferential direction; and a cross section of the annular groove is of lug-shaped.

12 Claims, 6 Drawing Sheets

ULTRASOUND-INDUCED POSITIONING TYPE PUNCTURE ASSEMBLY AND SLEEVE TYPE SMALL NEEDLE KNIFE

CROSS-REFERENCE TO RELATED APPLICATIONS

The present disclosure is a national stage application of International Patent Application No. PCT/CN2020/095853, which is filed on Jun. 12, 2020. The present disclosure claims priority to patent application No. 201920897676.3, filed to the China National Intellectual Property Administration on Jun. 14, 2019, entitled "Ultrasound-Induced Positioning Type Small Needle Knife" and patent application No. 201920896328.4, filed to the China National Intellectual Property Administration on Jun. 14, 2019, entitled "Protective Type Oriented-Cutting Small Needle Knife Assembly".

TECHNICAL FIELD

The present disclosure relates to a minimally invasive surgical apparatus for traditional Chinese medicine, in particular to an ultrasound-induced positioning type puncture assembly and a sleeve type small needle knife.

BACKGROUND

Acupotomy is mainly used for traumatic lesions of soft tissues and osteoarthropathy and is a closed lysis between surgical therapies and non-surgical therapies. A small needle knife is pierced deep into a treatment site to a lesion to quantitatively release a diseased tissue, so as to achieve the purpose of relieving pain and curing diseases. In practical applications, a tip of the small needle knife is always located in the patient's body, and an operator can only observe the specific position of the tip through ultrasound imaging.

In an art known to inventors, an outer wall of a puncture assembly of the small needle knife is usually provided with a plurality of triangular pyramid grooves (with a CCR technology, a cubic mirror technology) uniformly disposed along an outer circumferential surface or semicircular annular grooves disposed along an outer circumferential surface, so as to enhance ultrasonic reflection and form clear ultrasound images. However, due to a small diameter of the puncture assembly, it is difficult to machine the triangular pyramid grooves in the outer circumferential surface. For the semicircular annular grooves, side walls of sides of the semicircular annular grooves close to ultrasound development equipment will block ultrasonic echo, which is not conducive to the development, resulting in a high requirement for the configuration of ultrasound equipment and high price. Most equipment needs to be imported, and instruments have large volumes and are hard to move.

In addition, in the art known to inventors, a cutting edge is formed at a front end of the small needle knife. During the movement of the knife body, the cutting edge abuts against the diseased tissue and further cuts it. However, by the adoption of the small needle knife with the above structure, the cutting edge is exposed throughout the process before reaching the diseased tissue. Due to operational deviation and tissue variation, the cutting edge can easily injure surrounding nerves or blood vessels, causing irreparable injury to the patient. By using a forward, vertical cutting method, tissues with relatively high toughness and intensity are prone to detachment and are more difficult to cut.

SUMMARY

In view of the above analysis, some embodiments of the present disclosure provide an ultrasound-induced positioning type puncture assembly and a sleeve type small needle knife, and solves the problems, in the art known to inventors, that it is difficult to machine triangular pyramid grooves of the puncture assembly, side walls of sides of semicircular annular grooves close to ultrasound development equipment will block ultrasonic echo, a cutting edge of the small needle life can easily injure surrounding nerves or blood vessels, and cutting with a forward, vertical cutting method is relatively difficult to realize.

Some embodiments of the present disclosure are achieved through the following technical solutions:

Some embodiments of the present disclosure provide an ultrasound-induced positioning type puncture assembly, including a puncture needle core and a puncture sleeve sleeved on an outer side of the puncture needle core. A annular groove facing an ultrasound equipment probe is formed in an outer wall of the puncture sleeve along a circumferential direction of the puncture sleeve. A cross section of the annular groove along a radial direction of the puncture sleeve is of lug-shaped.

In some embodiments, the cross section of the annular groove along the radial direction of the puncture sleeve includes an arc edge and a straight edge connected with the arc edge; the straight edge is close to ultrasound development equipment; and the arc edge is close to a puncture end of the puncture assembly.

In some embodiments, an included angle between the straight edge and an axial line of the puncture sleeve is 45-60 degrees.

In some embodiments, a cutting edge is formed at a puncture end of the puncture needle core.

In some embodiments, the cutting edge is a single inclined plane or double inclined planes.

In some embodiments, a single inclined plane or double inclined planes is or are formed at a puncture end of the puncture sleeve.

Some embodiments of the present disclosure further provide a sleeve type small needle knife including a cutting assembly and the above puncture assembly. The cutting assembly includes a cutting needle knife and a cutting sleeve sleeved on an outer side of the cutting needle knife.

In some embodiments, a cutting edge is formed on a side surface of a cutting end of the cutting needle knife; the cutting end of the cutting sleeve is of arc-shaped; part or all of a side surface of the cutting sleeve is provided with a cutting seam.

In some embodiments, the cutting edge is a hook or a lateral edge.

In some embodiments, an operation end of the cutting sleeve is provided with an orientation identifier used for indicating an orientation of the cutting seam.

In some embodiments, the orientation identifier is arranged on the same side surface as the cutting seam and is located on the same straight line as the cutting seam.

In some embodiments, a movement limiting assembly is arranged between a cutting end of the cutting needle knife and a cutting end of the cutting sleeve, the movement limiting assembly is used for limiting a relative rotation between the cutting needle knife and the cutting sleeve in a movement process of the cutting needle knife and the cutting sleeve.

In some embodiments, the movement limiting assembly includes a movement groove and a movement protrusion inserted into the movement groove.

In some embodiments, a cutting limiting assembly is arranged between a cutting end of the cutting needle knife and a cutting end of the cutting sleeve and is used for limiting a relative rotation between the cutting needle knife and the cutting sleeve in a cutting process of the cutting needle knife.

In some embodiments, the cutting limiting assembly includes a cutting groove and a cutting protrusion inserted into the cutting groove.

Compared with the art known to inventors, some embodiments of the present disclosure can at least achieve one of the following beneficial effects:

a) In the ultrasound-induced positioning type puncture assembly provided by some embodiments of the present disclosure, the annular grooves on the outer wall of the puncture sleeve face the ultrasound equipment probe, and the cross sections of the annular grooves along the radial direction of the puncture sleeve are of lug-shaped. Compared to the semicircular annular grooves, the annular grooves are that the side walls close to the ultrasound equipment probe have relatively small inclination angles, so that blockage of the side walls of the annular grooves to ultrasonic waves can be reduced, relatively strong reflection of the ultrasonic waves can be ensured, clear ultrasound images can be formed, and a satisfactory development effect is achieved.

b) In the ultrasound-induced positioning puncture assembly provided by some embodiments of the present disclosure, the annular grooves disposed on the outer wall of the puncture sleeve are formed by continuous machining. Compared to the triangular pyramid grooves, the annular grooves are easy to machine and conductive for production. The induced positioning development requirement can be met with simple and portable ultrasound equipment, which is convenient for safe and effective promotion of technologies.

c) The sleeve type small needle knife provided by some embodiments of the present disclosure includes two assemblies, i.e., the puncture assembly and the cutting assembly. The puncture assembly is mainly used for puncturing and guidance, and the cutting assembly is mainly used for cutting a diseased tissue. The cutting end of the cutting sleeve of the cutting assembly is of arc-shaped, which is usually used for blunt dissection of tissues or nerves. This is only carried out between tissues. Furthermore, before reaching the diseased tissue, the cutting end of the cutting needle knife is always located in the cutting sleeve and in no contact with the tissue, so that injury to the surrounding nerves or blood vessels by the cutting edge is reduced, and an effective guarantee is provided for the patient.

d) In the sleeve type small needle knife provided by some embodiments of the present disclosure, since the cutting edge is formed on the side surface of the cutting end of the cutting needle knife, the diseased tissue is more easily cut by a lateral cutting method compared to the forward, vertical cutting method, which lowers the difficulty of the small needle knife therapy.

Other features and advantages of the present disclosure will be described in the following specification, and partly become obvious from the specification, or understood by implementing the present disclosure. The objectives and other advantages of the present disclosure can be realized and obtained through the structures specifically pointed out in the written specification and drawings.

BRIEF DESCRIPTION OF THE DRAWINGS

The drawings are only used for the purpose of illustrating specific embodiments, and are not considered as a limitation to the present disclosure. Throughout the drawings, the same reference signs represent the same components.

Figure 1:
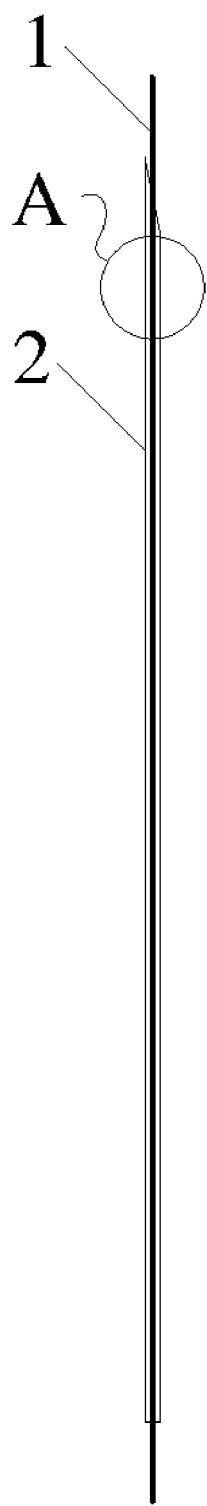
FIG. 1 is a schematic structural diagram of an ultrasound-induced positioning type puncture assembly of Embodiment I of the present disclosure, wherein a single inclined plane is formed at a puncture end of a puncture sleeve.

Reference signs in the drawings:
1: puncture needle core; 2: puncture sleeve; 3: annular groove; 31: arc edge; 32: straight edge; 4: cutting needle knife; 5: cutting sleeve; 6: cutting seam; 7: hook; 8: lateral edge; 9: orientation identifier.

DETAILED DESCRIPTION OF THE EMBODIMENTS

Some embodiments of the present disclosure will be specifically described in detail with reference to the accompanying drawings. The accompanying drawings constitute a part of the present disclosure and are used together with the embodiments of the present disclosure to explain the principle of the present disclosure.

Embodiment I

Figure 2:
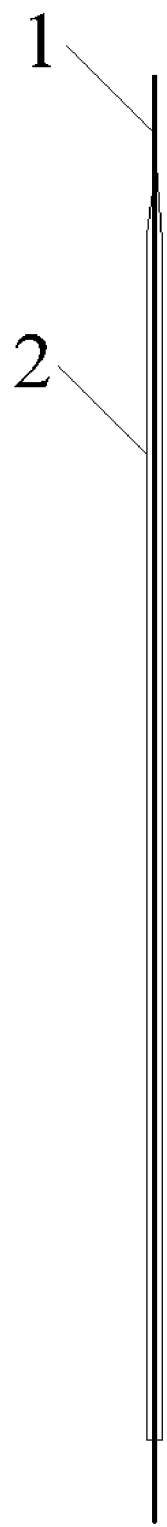
FIG. 2 is a schematic structural diagram illustrating that double inclined planes are formed at a puncture end of an ultrasound-induced positioning type puncture assembly of Embodiment I of the present disclosure.
Figure 3:
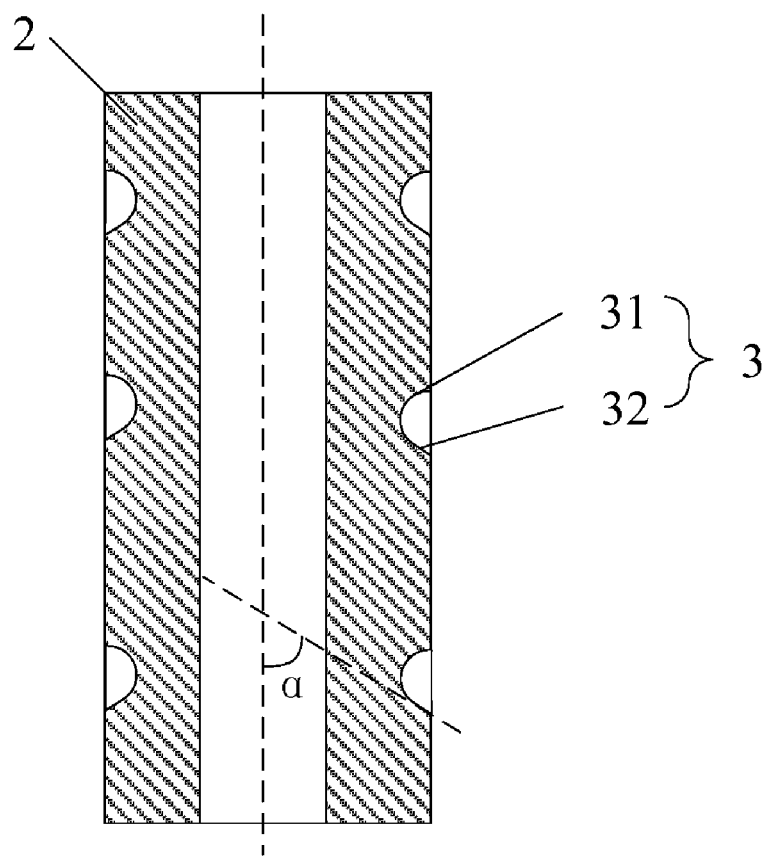
FIG. 3 is a partially enlarged diagram of FIG. 1.

Some embodiments of the present embodiment provide an ultrasound-induced positioning type puncture assembly, referring to FIG. 1 to FIG. 3, including a puncture needle core 1 and a puncture sleeve 2 sleeved on an outer side of the puncture needle core 1. An annular groove 3 facing an ultrasound equipment probe is formed in an outer wall of the puncture sleeve 2 along a circumferential direction of the puncture sleeve 2. A cross section of the annular groove 3 along a radial direction of the puncture sleeve 2 is of lug-shaped. In some embodiments, the annular groove 3 may be close to a puncture end of the puncture sleeve 2.

During the small needle knife therapy, firstly, the puncture assembly punctures a body surface of a patient, and the puncture end is made to be close to a diseased tissue.

Compared with an art known to inventors, the ultrasound-induced positioning type puncture assembly has the advantages that the annular groove 3 on the outer wall of the puncture sleeve 2 faces the ultrasound equipment probe, and the cross section of the annular groove 3 along the radial direction of the puncture sleeve 2 is of lug-shaped. Compared to semicircular annular grooves 3, the annular groove that a side wall close to the ultrasound equipment probe has a relatively small inclination angle, so that blockage of the side wall of the annular groove 3 to ultrasonic waves is reduced, relatively strong reflection of the ultrasonic waves can be ensured, clear ultrasound images can be formed, and a satisfactory development effect is achieved.

In addition, in the ultrasound-induced positioning puncture assembly provided by the present embodiment, a plurality of annular grooves 3 disposed on the outer wall of the puncture sleeve 2 are formed by continuous machining. Compared to triangular pyramid grooves, the annular grooves are easy to machine and conductive for production. The induced positioning development requirement can be met with simple and portable ultrasound equipment, which is convenient for safe and effective promotion of technologies.

In some embodiments, the cross section of the annular groove 3 along the radial direction of the puncture sleeve 2 includes an arc edge 31 and a straight edge 32 connected with the arc edge 31; the straight edge 32 is close to ultrasound development equipment; and the arc edge 31 is close to a puncture end of the puncture assembly. By the adoption of the above shape, the arc shape and the straight shape are simple and are easy to realize in a machining production process, thus further lowering the machining difficulty of the small needle knife.

Considering that an included angle between ultrasonic waves emitted by the ultrasound equipment probe and an axial line of the puncture sleeve 2 is 45-60 degrees, to further reduce the blockage of the side wall of the annular groove 3 to the ultrasonic waves, in some embodiments, an included angle between the straight edge 32 and the axial line of the puncture sleeve 2 may also be 45-60 degrees. That is, the straight edge 32 is basically parallel to the direction of the ultrasonic waves emitted by the ultrasound equipment probe, and demands for treating superficial and deep tissues are simultaneously met.

For the structure of the puncture needle core 1, in some embodiments, a cutting edge is formed at the puncture end of the puncture needle core 1. The cutting edge is used as a puncture surface so that the puncture end enters patient's body more easily. Furthermore, in some embodiments, in terms of a machining angle, a single inclined plane or double inclined planes is easy to machine, so the production cost of the above ultrasound-induced positioning type puncture assembly is appropriately reduced.

In some embodiments, a single inclined plane or double inclined planes may be formed at the puncture end of the puncture sleeve 2. The single inclined plane or double inclined planes is used as a puncture surface so that the puncture end enters patient's body more easily. Furthermore, in terms of a machining angle, a single inclined plane or double inclined planes are easy to machine, so the production cost of the above ultrasound-induced positioning type puncture assembly is appropriately reduced.

Embodiment II

Figure 4:
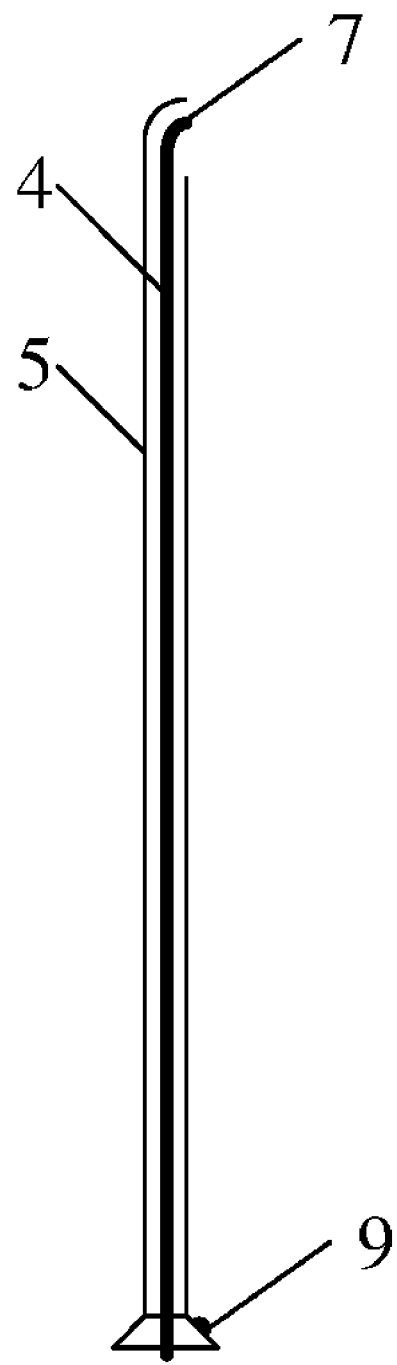
FIG. 4 is a schematic structural diagram of a cutting assembly in a sleeve type small needle knife of Embodiment II of the present disclosure.
Figure 5:
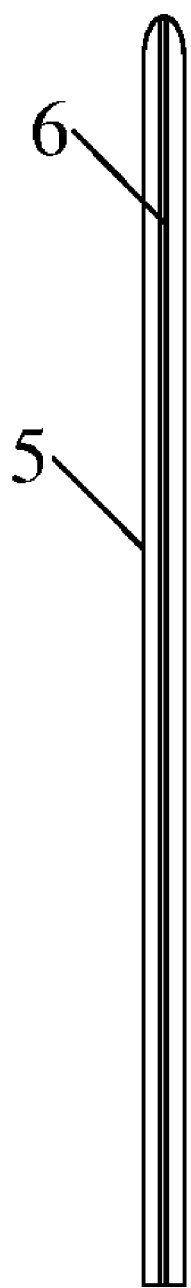
FIG. 5 is a schematic structural diagram illustrating that a cutting sleeve in a sleeve type small needle knife of Embodiment II of the present disclosure is overall laterally provided with a cutting seam.
Figure 6:
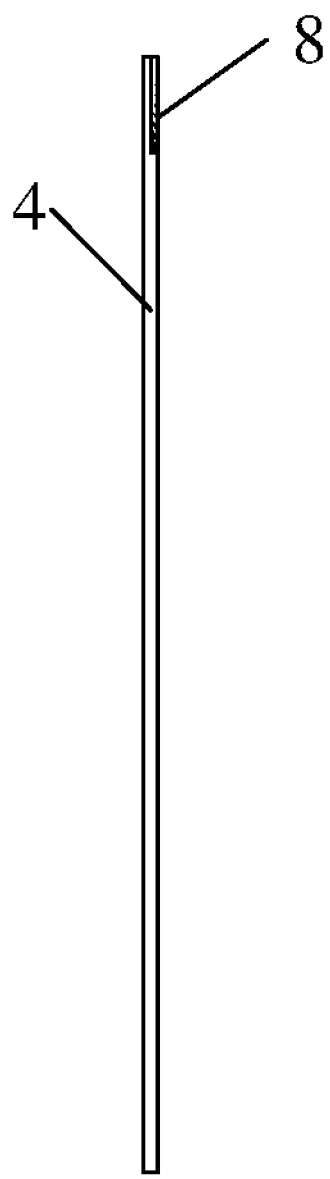
FIG. 6 is a schematic structural diagram illustrating that a lateral edge is formed at a cutting end of a cutting needle knife in a sleeve type small needle knife of Embodiment II of the present disclosure.

The present embodiment provides a sleeve type small needle knife, referring to FIG. 4 to FIG. 6, including a cutting assembly and the puncture assembly provided in Embodiment I. The cutting assembly is used for cutting a diseased tissue and includes a cutting needle knife 4 and a cutting sleeve 5 sleeved on an outer side of the cutting needle knife 4.

During the small needle knife therapy, firstly, the puncture assembly is used to puncture the patient's body surface, and the puncture end of the puncture sleeve 2 is made to be close to the diseased tissue. The puncture sleeve 2 is pulled out of the patient's body. At this time, the puncture needle core 1 is still in the patient's body. Then, an end of the puncture needle core 1 located outside the patient's body is threaded into the cutting sleeve 5, and the cutting sleeve 5 gets close to the diseased tissue under a guidance of the puncture needle core 1. Next, the puncture needle core 1 is withdrawn out of the cutting sleeve 5, and the cutting needle knife 4 is threaded into the cutting sleeve 5. At this time, a cutting edge at a cutting end of the cutting needle knife 4 is not in a cutting seam 6. Next, the cutting sleeve 5 and the cutting needle knife 4 are moved along a seam between tissues of the patient to the diseased tissue, and the diseased tissue is cut off with the cutting needle knife 4. Finally, the cutting sleeve 5 and the cutting needle knife 4 are pulled out to complete the small needle knife therapy.

Compared with an art known to inventors, the sleeve type small needle knife provided by the present embodiment includes two assemblies, i.e., the puncture assembly and the cutting assembly. The puncture assembly is mainly used for puncturing and guidance, and the cutting assembly is mainly used for cutting the diseased tissue. The beneficial effects of the present embodiment are basically the same as the beneficial effects of the ultrasound-induced positioning type puncture assembly provided by Embodiment I, so descriptions thereof are omitted here.

For the structures of the cutting needle knife 4 and the cutting sleeve 5 in the cutting assembly, in some embodiments, the cutting edge is formed on a side surface of the cutting end of the cutting needle knife 4. The cutting end of the cutting sleeve 5 is of arc-shaped, and part or all of a side surface is provided with a cutting seam 6. When the cutting assembly is used to cut the diseased tissue, first of all, the cutting needle knife 4 is threaded into the cutting sleeve 5. At this time, the cutting edge at the cutting end of the cutting needle knife 4 is not in the cutting seam 6. Then, the cutting sleeve 5 and the cutting needle knife 4 are moved along the seam between the tissues of the patient to the diseased tissue. The cutting needle knife 4 is rotated, so that the cutting end is inserted into the cutting seam 6 and the cutting edge is in contact with the diseased tissue. The cutting sleeve 5 and the cutting needle knife 4 are pulled to the outside, and the diseased tissue is cut off. Finally, the cutting needle knife 4 is rotated to enable the cutting edge of the cutting needle knife to be separated from the cutting seam 6, and the cutting sleeve 5 and the cutting needle knife 4 are pulled out to complete the small needle knife therapy. In this way, the cutting end of the cutting sleeve 5 of the cutting assembly is of arc-shaped, which is usually used for blunt dissection of tissues or nerves. This is only carried out between tissues. Furthermore, before reaching the diseased tissue, the cutting end of the cutting needle knife 4 is always located in the cutting sleeve 5 and in no contact with the tissue, so that injury to surrounding nerves or blood vessels by the cutting edge is reduced, and an effective guarantee is provided for the patient. In addition, since the cutting edge is formed on the side surface of the cutting end of the cutting needle knife 4, the diseased tissue is more easily cut by a lateral cutting method compared to the forward, vertical cutting method, which lowers the difficulty of the small needle knife therapy.

For the structure of the cutting end of the cutting needle knife 4, in some embodiments, a hook 7 or a lateral edge 8 is formed on the side surface of the cutting end and used as the cutting edge. When the structure with the hook 7 is used to cut the diseased tissue, the cutting sleeve 5 and the cutting needle knife 4 are pulled to the outside, and the hook 7 can break the diseased tissue. Compared to the lateral edge 8, it is easier to operate, thus further lowering the difficulty of the small needle knife therapy.

Considering that only one side surface of the cutting sleeve 5 is provided with the cutting seam 6, to enable the operator to be able to know the orientation of the cutting seam 6 in real time, in some embodiments, an operation end of the cutting sleeve 5 is provided with an orientation identifier 9 (such as straight lines or protrusions in different colors) used for indicating the orientation of the cutting seam 6. It can be understood that the orientation identifier 9 may be arranged on the same side surface of the cutting seam 6 and located on the same straight line as the cutting seam 6. In a cutting process, the operator may know the orientation of the cutting seam 6 through the orientation identifier 9, so that the cutting seam 6 may be aligned with the diseased tissue for accurate cutting.

It is worth noting that in a movement process of the cutting sleeve 5 and the cutting needle knife 4, the cutting edge at the cutting end of the cutting needle knife 4 needs to be always kept out of the cutting seam 6. In some embodiments, to avoid the rotation of the cutting needle knife 4 from exposing the cutting edge, a movement limiting assembly is arranged between the cutting end of the cutting needle knife 4 and the cutting end of the cutting sleeve 5 and used for limiting a relative rotation between the cutting needle knife 4 and the cutting sleeve 5 in their movement process. Under the limitation from the movement limiting assembly, the relative rotation between the cutting needle knife 4 and the cutting sleeve 5 is avoided, so that the cutting edge at the cutting end of the cutting needle knife 4 can be always kept out of the cutting seam 6.

In some embodiments, the movement limiting assembly includes a movement groove and a movement protrusion inserted into the movement groove.

It is also worth noting that in a process of cutting the diseased tissue, the rotation between the cutting needle knife 4 and the cutting sleeve 5 will also cause adverse influence on the small needle knife therapy. Therefore, a cutting limiting assembly is arranged between the cutting end of the cutting needle knife 4 and the cutting end of the cutting sleeve 5 and used for limiting the relative rotation between them in the cutting process of the cutting needle knife 4.

In some embodiments, the cutting limiting assembly includes a cutting groove and a cutting protrusion inserted into the cutting groove.

In some embodiments, when the cutting end of the cutting needle knife 4 and the cutting end of the cutting sleeve 5 need movement limitation and cutting limitation at the same time, one comprehensive limiting protrusion and two comprehensive limiting grooves are arranged between the two cutting ends. One of the two comprehensive limiting grooves is used for movement limitation, and the other comprehensive limiting groove is used for cutting limitation. The two comprehensive limiting grooves are distinguished by coating different colors, such as red and blue.

The foregoing descriptions are merely some specific implementation modes of the present disclosure, but the protection scope of the present disclosure is not limited thereto. Changes or replacements easily thought by any person skilled in the art within the technical scope disclosed in the present disclosure shall fall within the protection scope of the present disclosure.

What is claimed is:

1. A sleeve type small needle knife comprising a cutting assembly and an ultrasound-induced positioning type puncture assembly, wherein the ultrasound-induced positioning type puncture assembly comprises:
   a puncture needle core; and
   a puncture sleeve sleeved on an outer side of the puncture needle core, wherein an annular groove facing an ultrasound equipment probe is formed in an outer wall of the puncture sleeve along a circumferential direction of the puncture sleeve; and a cross section of the annular groove along a radial direction of the puncture sleeve comprises an arc edge and a straight e connected with the are edge; the straight edge is close to ultrasound development equipment; and the arc edge is close to a puncture end of the puncture assembly;
   the cutting assembly comprises a cutting needle knife and a cutting sleeve sleeved on an outer side of the cutting needle knife;
   wherein a cutting edge is formed on a side surface of a cutting end of the cutting needle knife; a cutting end of the cutting sleeve is of arc-shaped; and part of all of a side surface of the cutting sleeve is provided with a cutting seam.

2. The e small needle knife as claimed in claim 1, wherein an included angle between the straight edge and an axial line of the puncture sleeve is 45-60 degrees.

3. The sleeve type small needle knife as claimed in claim 1, wherein a cutting edge is formed at a puncture end of the puncture needle core.

4. The sleeve type small needle knife as claimed in claim 3, wherein the cutting edge is a single inclined plane or double inclined planes.

5. The sleeve type small needle knife as claimed in claim 1, wherein a single inclined plane or double inclined planes is or are formed at a puncture end of the puncture sleeve.

6. The sleeve type small needle knife as claimed in claim 1, wherein the cutting edge is a hook or a lateral edge.

7. The sleeve type small needle knife as claimed in claim 1, wherein an operation end of the cutting sleeve is provided with an orientation identifier used for indicating an orientation of the cutting seam.

8. The sleeve type small needle knife as claimed in claim 7, wherein the orientation identifier is arranged on the same side surface as the cutting seam and is located on the same straight line as the cutting seam.

9. The sleeve type small needle knife as claimed in claim 1, wherein a movement limiting assembly is arranged between a cutting end of the cutting needle knife and a cutting end of the cutting sleeve, wherein the movement limiting assembly is used for limiting a relative rotation between the cutting needle knife and the cutting sleeve in a movement process of the cutting needle knife and the cutting sleeve.

10. The sleeve type small needle knife as claimed in claim 9, wherein the movement limiting assembly comprises a movement groove and a movement protrusion inserted into the movement groove.

11. The sleeve type small needle knife as claimed in claim 1, wherein a cutting limiting assembly is arranged between a cutting end of the cutting needle knife and a cutting end of the cutting sleeve and is used for limiting a relative rotation between the cutting needle knife and the cutting sleeve in a cutting process of the cutting needle knife.

12. The sleeve type small needle knife as claimed in claim 11, wherein the cutting limiting assembly comprises a cutting groove and a cutting protrusion inserted into the cutting groove.

* * * * *